United States Patent [19]

Cohen

[11] Patent Number: 5,352,232

[45] Date of Patent: * Oct. 4, 1994

[54] METHOD FOR USING DETACHABLE TIP VALVULOTOME

[75] Inventor: Donald Cohen, Irvine, Calif.

[73] Assignee: Endovascular, Inc., Costa Mesa, Calif.

[*] Notice: The portion of the term of this patent subsequent to Feb. 8, 2011 has been disclaimed.

[21] Appl. No.: 120,039

[22] Filed: Sep. 10, 1993

Related U.S. Application Data

[62] Division of Ser. No. 895,090, Jun. 8, 1992, Pat. No. 5,284,478.

[51] Int. Cl.$^5$ ............................................. A61B 17/32
[52] U.S. Cl. ...................................... 606/159; 606/15
[58] Field of Search .......................... 606/159, 15, 16; 128/898

[56] References Cited

U.S. PATENT DOCUMENTS

| | | | |
|---|---|---|---|
| 3,837,345 | 9/1974 | Matar | 606/159 |
| 4,175,545 | 11/1979 | Termanini | |
| 4,493,321 | 1/1985 | Leather | 606/159 |
| 4,528,982 | 7/1985 | Wellenstam | 606/159 |
| 4,574,781 | 3/1986 | Chin | 606/159 |
| 4,576,162 | 3/1986 | McCorkle | 606/159 |
| 4,655,217 | 4/1987 | Reed | 606/159 |
| 4,739,760 | 4/1988 | Chin et al. | |
| 4,765,332 | 8/1988 | Fischell et al. | 128/305 |
| 4,768,508 | 9/1988 | Chin et al. | 606/159 |
| 5,026,383 | 6/1991 | Nobles | 606/159 |
| 5,087,264 | 2/1992 | Miller et al. | 606/159 |

FOREIGN PATENT DOCUMENTS

| | | |
|---|---|---|
| 3717926 | 12/1983 | Fed. Rep. of Germany |
| 8304174 | 12/1983 | PCT Int'l Appl. |
| 9101689 | 2/1991 | World Int. Prop. O. ........... 606/159 |
| 9112773 | 9/1991 | World Int. Prop. O. ........... 606/159 |

OTHER PUBLICATIONS

"In Situ Saphenous Vein Bypass: 1962 to 1987" Connolly, *American Journal* of Surgery Jul. 1987.
"Instrumental Evolution of the Valve Incision Method of in situ Sapaneous Vein Bypass," Leather et al. *Journal of Vascular Surgery*, Jan. 1984.
Publication Announcement: in situ Bypass Grafting by Dr. LeMaitre published by Vascutech Inc. 1987.
Advertisement: Leather in situ valve cutter kit by AHS Corp., Jun. 1985.
Advertisement: Hall Vein Stripper by Cabot Limited Apr. 1986.
Sales Material: Vascutech Inc.–The LeMatire Valvulotome System, Jun. 1987.

*Primary Examiner*—Michael H. Thaler
*Attorney, Agent, or Firm*—John L. Rogitz

[57] ABSTRACT

An optical valvulotome having a replaceable blade head for in situ cutting of venous valves has a catheter that can be pushed through a vein. An anchor is attached to the catheter, and a cutting head can be releasably engaged with the anchor to cut the valves as the catheter is pushed through the vein. The cutting head has two spaced apart cutting blades that form a light passageway between the blades. An optical fiber is disposed in the catheter for collecting light from the light passageway between the blades, and the optical fiber is engaged with a display apparatus for displaying a video image of the blades and vein as the catheter is pushed through the vein. The catheter can be retrieved from the vein, and the cutting head easily disconnected from the anchor and replaced with another cutting head having a size larger or smaller than the first head, as appropriate for the changing width of the lumen of the vein.

1 Claim, 2 Drawing Sheets

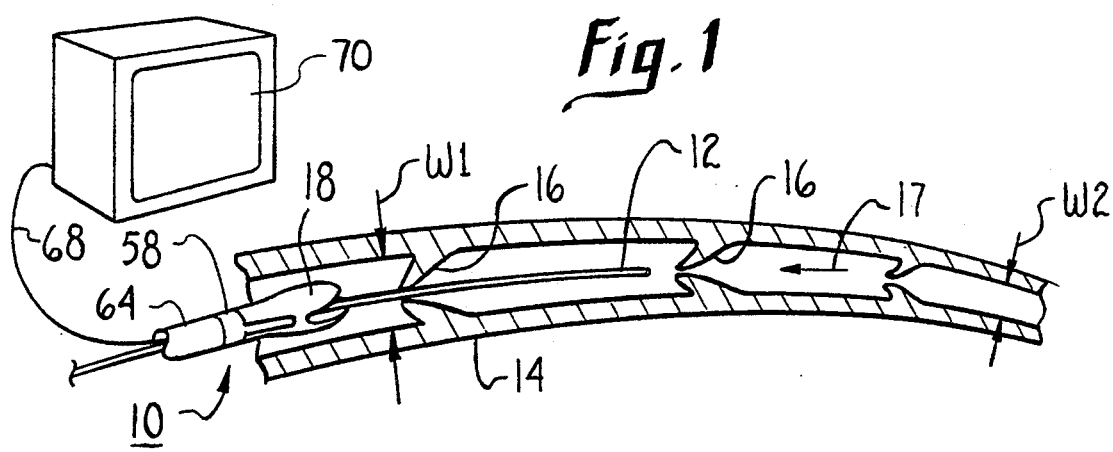
Fig. 1
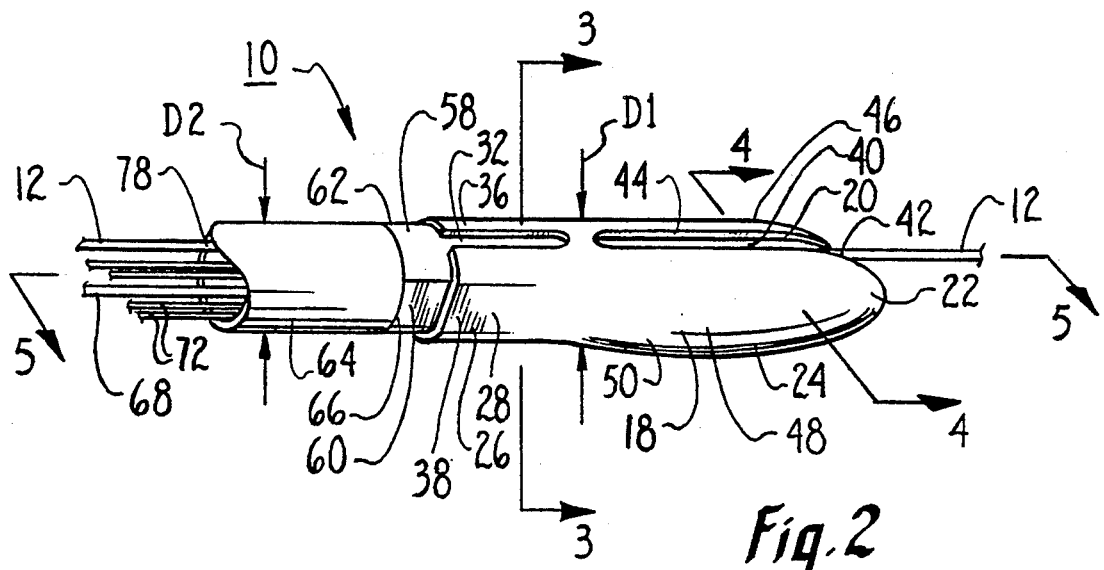
Fig. 2
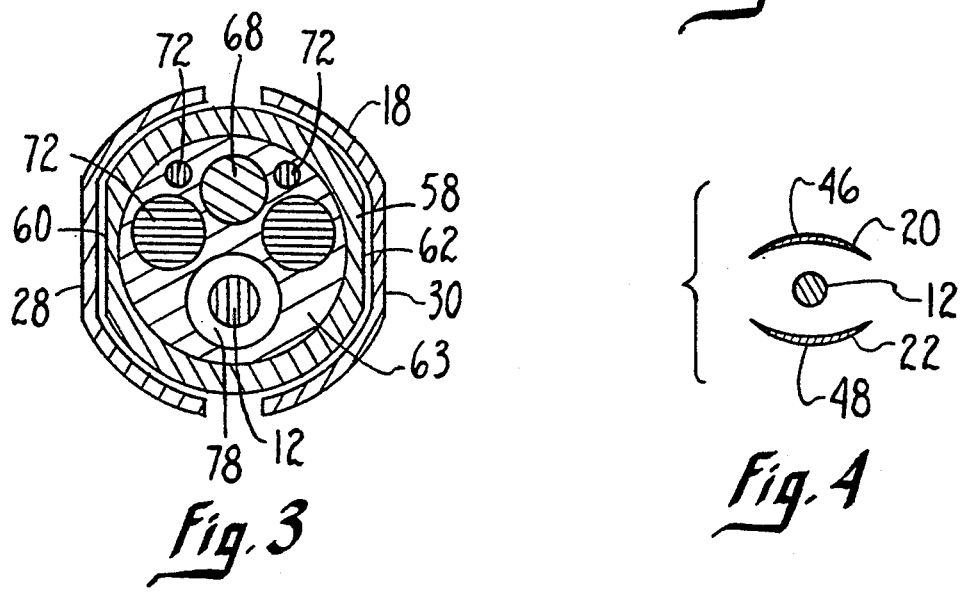
Fig. 3
Fig. 4

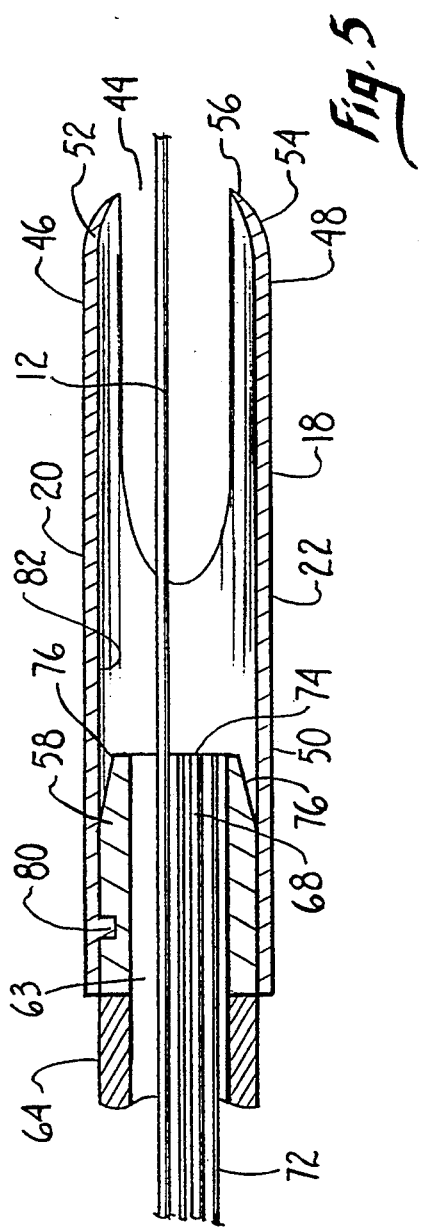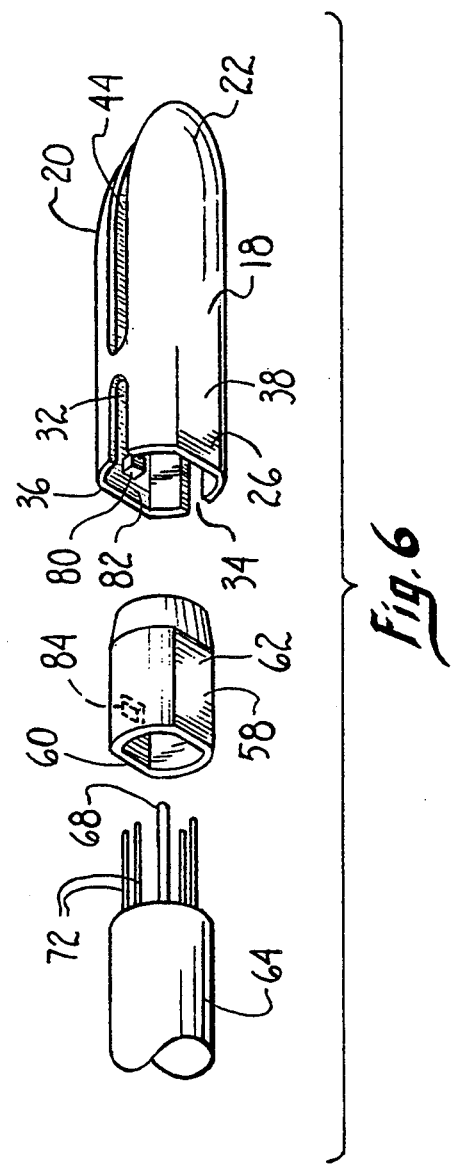

5,352,232

METHOD FOR USING DETACHABLE TIP VALVULOTOME

The present application is a divisional application of and claims priority from co-pending U.S. patent application Ser. No. 07/895,090, filed Jun. 8, 1992 now U.S. Pat. No. 5,284,478.

FIELD OF THE INVENTION

The present invention relates generally to methods and apparatus for cutting valves within a vein, and more specifically to methods and apparatus for cutting venous valves during in situ saphenous vein bypass.

BACKGROUND OF THE INVENTION

In situ saphenous vein bypass is a procedure in which the saphenous vein in a human leg, which normally returns blood from the ankle upwardly through the leg, takes over the function of the femoral artery in the leg after the femoral artery has become too occluded, or otherwise impaired, to transport the flow of blood required of it.

When the saphenous vein is to be used to take over the function of the femoral artery, it becomes necessary to cut open the series of one-way valves which exist in the saphenous vein. These one-way valves in normal functioning prevent reverse flow of blood to the saphenous vein. In other words, the one-way valves permit flow of blood in the saphenous vein from the ankle to the thigh but do not permit the flow of blood in the opposite direction, which is otherwise required when the saphenous vein is to function in place of the femoral artery.

Accordingly, various valve strippers have been developed for cutting venous valves in situ in a patient's saphenous vein. Some of these valve strippers use a valve cutter which is passed through the vein in a direction opposite to the normal direction of venous blood flow through the vein to sever the valves. Examples of such valve cutters include the LaMaitre valvulotome, made by Vascutech of Massachusetts; the Hall vein stripper, made by Cabot Ltd. of High Wycombe, England; and the Leather valve cutter, made by American V. Mueller of Chicago, Ill.

Unfortunately, the valve strippers noted above operate blindly. Specifically, they are passed through the vein by a surgeon who does not directly observe the stripper or vein as the cutters operate. It will accordingly be appreciated that while such devices can perform quite satisfactorily in the hands of an experienced cardiovascular surgeon operating on a vein which does not have complications, blind incision of the valves has serious risks. For example, if the cutter's path veers off course into the side wall of the vein (this can happen without the ability to observe the vein directly), the blades can cut the delicate endothelial lining of the vein with serious adverse consequences. Also, side branches, i.e., veins entering the main vein from the side, may be caught by the valve cutter and torn open. This also causes serious injury.

To overcome the disadvantages of the so-called blind valve strippers noted above, an apparatus and method have been disclosed in U.S. Pat. No. 5,026,383 to Nobles that provides a fiber optic scope which is mounted in a valve cutter to view the valve cutter and adjacent tissue as the valve cutter travels through the vein. As envisioned by the Nobles device, a pulling catheter is inserted into the saphenous vein near the ankle and is passed in the normal direction of venous blood flow through the saphenous vein until its tip emerges through an exit opening created in the vein. A cutting catheter that has a cutting head comprising two spaced apart blades is then attached to the pulling catheter. Then, the pulling catheter can be pulled reversibly through the vein to cause the cutting blades to cut through the valves. The surgeon can make observations of the vein during the passage of the cutting catheter through the vein by means of the fiber optic scope.

In accordance with the Nobles device, the cutting catheter can be easily and quickly engaged with the pulling catheter. Also, the cutting head disclosed in the above-referenced Nobles patent is shaped to generally conform to the contours of the vein wall, thus reducing the risk that the cutting blade of the Nobles device will inadvertently cut the wall of the vein.

The Nobles device is generally satisfactory for the purposes for which it is intended. It happens, however, that the pulling catheter of devices such as the Nobles device can occasionally be difficult to pull through a saphenous vein. Thus, the present invention recognizes that it is desirable to provide a valvulotome that can be pushed through a saphenous vein.

Furthermore, the lumen of a saphenous vein ordinarily tapers gradually inwardly, from the thigh to the ankle. Thus, it will be appreciated that a cutting head which is large enough to efficaciously cut valves in a saphenous vein in the thigh of a patient may be too large to be pushed through the relatively narrower portion of the saphenous vein near the ankle of a patient. In other words, the present invention recognizes that a cutting blade, having only a single size, cannot optimally be used to cut valves in the saphenous vein, both in the thigh of a patient and near the ankle of a patient.

Accordingly, it is an object of the present invention to provide an optical valvulotome which has a cutting head that is detachable from the remainder of the valvulotome.

Another object of the present invention is to provide an optical valvulotome which can provide a video display of the interior of the vein during an in situ saphenous vein bypass procedure.

An additional object of the present invention is to provide an optical valvulotome which is easy to use and cost effective to manufacture.

SUMMARY OF THE INVENTION

A valvulotome for cutting venous valves in a blood vessel includes a catheter which is sufficiently flexible to follow the contour of the blood vessel when the catheter is passed through the blood vessel. Also, the catheter is sufficiently axially rigid to permit the catheter to be pushed through the blood vessel.

In accordance with the present invention, the catheter has a distal end, and an anchor is fixedly attached to the catheter at the distal end of the catheter. The anchor has an open distal end. In turn, a cutting head, which includes a pair of cutting blades, is detachably connected to the anchor near the open distal end of the anchor. The cutting blades have sharp cutting edges and are shaped to engage and cut through venous valve cusps when the cutting blades are aligned with the valves. Further, the blades have exterior sides that are contoured to generally follow the curvature of the interior walls of the blood vessel.

As envisioned by the present invention, the blades are disposed relative to the open distal end of the anchor to establish a light passageway from the open distal end of the anchor to the interior sides of the blades and to adjacent regions within the vein. Additionally, a viewing scope is mounted within the catheter in light communication with the light passageway for generating an image of the interior sides of the blades and the adjacent regions within the vein.

In a preferred embodiment of the present invention, the cutting head has a hollow proximal segment which is snappingly engageable with the anchor. In the preferred embodiment, the cutting head defines a longitudinal axis and has two slots that are opposed to each other on the cutting head. The slots extend generally parallel to the longitudinal axis of the cutting head and establish first and second portions of the proximal segment of the cutting head.

Further, the cutting head includes a detent formed on the inside surface of the cutting head and protruding inwardly from the inside surface. In turn, the anchor is formed with an opening which receives the detent on the cutting head.

Thus, the cutting head has an operating configuration, wherein the first and second portions of the cutting head closely engage the anchor in a surrounding relationship therewith, and the detent is engaged with the slot. Also, the cutting head has a replacement configuration, wherein the first and second portions of the cutting head are spaced from the anchor, and the detent is distanced from the slot, to permit disengaging the cutting head from the anchor.

As further envisioned by the present invention, the cutting head is materially biased to the operating configuration. The replacement configuration of the cutting head, however, can be established by urging the cutting blades toward each other. If desired, a key can be formed on the cutting head and a corresponding key way formed on the anchor for receiving the key therein to prevent rotational movement of the cutting head relative to the anchor.

Additionally, in one presently preferred embodiment each cutting blade has an external contour which closely conforms to the shape of the vein to reduce the risk of inadvertently cutting the vein wall. More particularly, each blade has a contour which, when viewed in a plan direction perpendicular to the axis of the blade head, has a parabolic-like shape. Stated differently, each blade has an edge that is parabola-shaped. Also, each cutting blade has an outer edge which, when viewed side on relative to the plan view, is flush with the cylindrical outer surface of the cutting head, except for a region adjacent to the tip, which is curved radially inwardly. Consequently, the risk of gouging the blood vessel in the event of a glancing contact with the wall of the blood vessel by the cutting blade is reduced.

The catheter of the present invention includes a guide wire lumen, and the guide wire lumen is engageable with the guide wire for pushing the catheter over the wire inside the vein.

In another aspect of the present invention, an apparatus for in situ cutting of valves within a blood vein, when pushed through the vein in a direction opposite to the normal flow of blood through the vein, includes an elongate pushing member that has an open distal end. A cutting head is detachably connected to the pushing member such that the cutting head can be selectively engaged and disengaged with the pushing member without unduly damaging the cutting head or pushing member.

As intended by the present invention, the cutting head includes a distal segment that has at least a pair of cutting blades spaced from each other. The blades have exterior sides which are contoured to generally follow the curvature of the interior walls of the blood vessel. In accordance with this aspect of the present invention, the blades are disposed relative to the open distal end of the anchor to establish a light passageway from the open distal end to the interior sides of the blades and to regions that are adjacent to the interior sides of the blades.

An optical fiber is mounted on the pushing member and has a distal end positioned adjacent to the distal end of the pushing member. Accordingly, the optical fiber can collect light from the distal end of the pushing member and direct the light to a viewing apparatus for displaying an image of the interior sides of the blades and adjacent regions within the vein on the viewing apparatus.

In yet another aspect of the present invention, an apparatus for the in situ cutting of venous valves has a catheter which has axial strength sufficient for pushing the catheter through a vein. The catheter has an optical fiber disposed therein, and a cutting head having a pair of cutting blades and a light passageway therebetween is also provided. An anchor is attached to the catheter for releasably holding the cutting head onto the catheter. As envisioned by the present invention, the optical fiber is in light communication with the light passageway for collecting light from the light passageway and directing the light to a display apparatus for displaying a video image of at least a portion of the light passageway thereon.

In still another aspect of the present invention, a method for cutting venous valves in situ within a vein includes the steps of making an entry opening into the vein. A cutting blade is connected to a pushing member and the pushing member is operably engaged with an optical scope. The pushing member is then advanced into the vein through the opening in a direction opposite to normal venous blood flow to cut the venous valves with the cutting blade and to generate an image of the inside of the vein. The pushing member is then removed from the vein, and the cutting blade disconnected from the pushing member without substantially damaging the cutting blade and pushing member. Another cutting blade can then be connected to the pushing member without substantially damaging the cutting blade and pushing member.

The advantages and features of the present invention will be better understood by the following description when considered in conjunction with the accompanying drawings in which:

BRIEF DESCRIPTION OF THE DRAWINGS

FIG. 1 is a schematic view of the valvulotome of the present invention, showing the valvulotome being advanced over a guide wire through a saphenous vein of a human patient;

FIG. 2 is a perspective view of the valvulotome of the present invention;

FIG. 3 is a cross-sectional view of the valvulotome of the present invention, as seen along the line 3—3 in FIG. 2;

FIG. 4 is a cross-sectional view of the valvulotome of the present invention, as seen along the line 4—4 in FIG. 2;

FIG. 5 is a cross-sectional view of the valvulotome of the present invention, as seen along the line 5—5 in FIG. 2; and FIG. 6 is an exploded perspective view of the valvulotome of the present invention.

DETAILED DESCRIPTION

Referring initially to FIG. 1, a valvulotome is shown, generally designated 10. As shown, the valvulotome 10 can be advanced over a guide wire 12 into a saphenous vein 14 incident to a surgical procedure referred to as in situ saphenous vein bypass surgery. In saphenous vein bypass surgery, the saphenous vein 14 of a patient is used as a shunt for carrying blood around a femoral artery which has become clogged or otherwise unusable.

The saphenous vein 14, however, which normally carries venous blood from the ankle of the patient upwardly to the thigh region, i.e., in the direction indicated by the arrow 17, cannot merely be grafted onto the femoral artery to replace the femoral artery in carrying arterial blood from the thigh region to the lower regions of the leg, i.e., opposite to the direction indicated by the arrow 17. This is because a plurality of one-way valves 16 exist in the saphenous vein 14 which ordinarily permit blood to flow only upwardly through the vein, i.e., in the direction indicated by the arrow 17, not downwardly. Accordingly, as shown in FIG. 1, the valvulotome 10 can be used to cut the valves 16, to thereby permit the saphenous vein 14 to carry arterial blood to the lower regions of the leg.

FIG. 1 also shows that saphenous vein 14 has a width W1 near a portion of the saphenous vein 14 in the thigh of the patient which is greater than a width W2 near a portion of the saphenous vein 14 that is in the ankle of the patient. In other words, the inside lumen of the vein 14 gradually narrows from the thigh of the patient to the ankle of the patient. Typical dimensions for the widths W1 and W2 in an adult patient are about five millimeters (5 mm) and two millimeters (2 mm), respectively.

Accordingly, the skilled artisan will appreciate that a valvulotome which is large enough to cut venous valves 16 in the saphenous vein in the thigh of the patient may be too large to safely cut venous valves in the saphenous vein in the ankle of the patient, without the risk of cutting the saphenous vein itself. The present invention overcomes this problem by providing a valvulotome 10 which can be operably engaged with one of a plurality of detachable cutting heads, as more fully disclosed below. The cutting heads have various sizes as appropriate for the particular portion of the vein 14 in which it is desired to cut a venous valve 16.

Now referring to FIG. 2, the details of the present invention can be seen. As shown, the valvulotome 10 includes a hollow cutting head 18, and the cutting head 18 has a pair of opposed cutting blades 20, 22 formed on a distal segment 24 of the cutting head 18. Also, the cutting head 18 has a proximal segment 26.

In cross-reference to FIGS. 2 and 3, the proximal segment 26 of the cutting head 18 has a generally cylindrical shape, except for opposed keyed surfaces 28, 30 which are flat, for purposes to be disclosed below. Additionally, the proximal segment 26 of the cutting head 18 has two slots 32, 34 (only slot 32 shown in FIG. 2) formed therein, diametrically opposed to each other. The slots 32, 34 divide the proximal portion 26 into first and second proximal half portions 36, 38.

FIG. 2 shows that each cutting blade 20, 22 has a respective sharpened cutting edge 40, 42. The cutting edges 40, 42 together form a U-shaped opening 44. Thus, the cutting edges 40, 42 of the cutting blades 20, 22 are shaped to cut through the venous valves 16 when the cutting blades 20, 22 are aligned with the valves 16.

It can be appreciated in cross-reference to FIGS. 2 and 4 that the blades 20, 22 are spoon-shaped. Specifically, the blades 20, 22 have respective exterior surfaces 46, 48 which are curvilinearly contoured to generally follow the curvature of the interior walls of the vein 14. Also, as can be appreciated in reference to FIG. 2, the cutting edges 40, 42 of the blades 20, 22 are parabolic shaped. Stated differently, the cutting edges 40, 42 of the blades 20, 22 have external contours which, when viewed along a direction perpendicular to the outer surfaces 46, 48 of the blades 20, 22, i.e., perpendicular to the axis of the cutting head 18, have parabolic-like shapes which blend with an outer surface 50 of the cutting head 18.

With further regard to the shape of the blades 20, 22, FIG. 5 shows that the outer surfaces 46, 48 of the blades 20, 22 are generally flush with the outer surface 50 of the cutting head 18 except for respective regions 52, 54 near a distal end 56 of the cutting head 18, which are curved radially inwardly as shown.

As a consequence of the shape of the blades 20, 22, the risk of gouging the vein 14, in the event of a glancing contact of the cutting head 18 with the wall of the vein 14 is reduced. "Glancing contact" means contact between one of the blades 20, 22 and the wall of the vein 14, wherein one of the blades 20, 22 moves against the vein 14 at an angle of less than about 15°. Contacts between the blades 20, 22 and the vein 14 at greater angles are less likely because the observations made through the scope enable the surgeon to avoid such contacts, and because of the generally parallel alignment of the vein and the cutting head 18.

Preferably, the cutting head 18 is a generally cylindrical hollow one-piece structure that has an outside diameter D1 ranging from about one and nine-tenths millimeters (1.9 mm) to three millimeters (3.0 mm). As envisioned by the present invention, the cutting head 18 can be machined or molded from a plastic capable of having sharp edges formed in it, e.g., high density injection molded nylon. Other materials which may be used include polysulfone, polyethersulfone, and stainless steel. The shape and construction of the blades 20, 22 are described in U.S. Pat. No. 5,026,383 to Nobles, which is incorporated herein by reference.

In reference to FIG. 2, the cutting head 18 can be slid over an anchor 58 to fixedly engage the cutting head 18 with the anchor 58. As intended by the present invention, the cutting head 18 is releasably engaged with the anchor 58. In other words, the cutting head 18 is selectively detachably engaged with the anchor 58.

As shown, the anchor 58 is generally cylindrically shaped, except for flat keyway surfaces 60, 62, and is filled with an epoxy 63, for purposes to be shortly disclosed. As can be appreciated in cross-reference to FIGS. 2 and 3, the keyway surfaces 60, 62 of the anchor 58 engage the keyed surfaces 28, 30 of the cutting head 18 to prevent rotational motion of the cutting head 18 relative to the anchor 58, and to ensure that the cutting head 18 is properly aligned with the anchor 58.

In the presently preferred embodiment, the cutting head 18 is snappingly engaged with the anchor 58 to hold the cutting head 18 onto the anchor 58. Thus, the cutting head 18 is slid over the anchor 58 in a close surrounding relationship therewith and then snappingly engaged with the anchor 58. It is to be understood, however, that other means for releasably engaging the cutting head 18 with the anchor 58 may be used. For example, the cutting head 18 may be threadably engaged with an anchor.

Still referring to FIG. 2, the anchor 58 is attached to a catheter 64 at a butt joint 66 which is formed between the catheter 64 and anchor 58. More specifically, the anchor 58 and catheter 64 are adhesively joined end-to-end. Together, the anchor 58 and catheter 64 establish a pushing member for pushing the cutting head 18 through the vein 14.

While FIG. 2 shows that the anchor 58 is connected to the catheter 64 at a butt joint 66, it is to be understood that the anchor 58 may be connected to the catheter 64 by other means. For example, an anchor can be connected to a catheter by means of an overlapping, i.e., lap joint (not shown). The skilled artisan will appreciate, however, that by connecting the anchor 58 to the catheter 64 end-to-end at the butt joint 66, the overall diameter of the valvulotome 10 can be minimized.

In one presently preferred embodiment, the catheter 64 has a diameter D2 of about 1.7 mm. Suitable structures which can be used for the catheter 64 include an angioscope or endoscope made by Neuro Navigational Corporation having an outside diameter D2 of about 1.7 mm.

Such scopes, which are well-known in the art, ordinarily include a fiber optic image fiber 68 which can be operably engaged to a video display apparatus 70 (FIG. 1) for displaying an image of an object. Also, such scopes ordinarily include a plurality of illumination fibers 72.

With particular regard to the image fiber 68, the image fiber 68 extends through the catheter 64 and into the anchor 58. As can best be appreciated in reference to FIG. 5, a distal end 74 of the image fiber 68 is positioned adjacent a distal end 76 of the anchor 58. As shown, the distal end 76 is bevelled, for purposes to be shortly disclosed. Moreover, as shown best in cross-reference to FIGS. 3 and 5, the image fiber 68 is supported in the anchor 58 by the epoxy 63.

Also, the illuminating fibers 72 extend into the anchor 58. Thus, the opening 44 of the cutting head 18 essentially establishes a light passageway from the distal end 76 of the anchor 58 to the interior of the cutting head 18. Also, the opening 44 of the cutting head 18 essentially establishes a light passageway from the distal end 76 of the anchor 58, to regions of the vein 14 which are adjacent to the cutting head 18.

In accordance with the present invention, the epoxy 63 is deposited between the image fiber 68, illuminating fibers 72, and anchor 58, to hold the fibers 68, 72 within the anchor 58 and to further bond together the catheter 64 and anchor 58.

Referring again to FIGS. 2 and 3, in one presently preferred embodiment the catheter 64 includes a lumen 78 through which the guide wire 12 can be positioned and slidably engaged with the lumen 78. As shown in FIG. 2, the guide wire 12 extends through the lumen 78 and also extends through the anchor 58 and cutting head 18. Thus, the valvulotome 10 can be slidably engaged with the guide wire 12 and advanced over the wire 12 into the vein 14. If desired, the catheter 64 can be formed with other lumens (not shown) through which flushing fluid can be directed and from which debris from the operating site may be evacuated.

Referring now to FIG. 6, the means by which the cutting head 18 is snappingly engaged with the anchor 58 can be seen. As shown, the cutting head 18 has a detent 80 formed on an inner surface 82 of the cutting head 18. The detent 80 can snappingly engage an opening 84 which is formed in the wall of the anchor 58.

It is to be understood that FIGS. 2 and 5 depict an engagement configuration of the cutting head 18, i.e., with the cutting head 18 engaged with the anchor 58. It is to be further understood that the cutting head 18 is biased into the operating configuration shown in FIGS. 2 and 5. As can be appreciated in cross-reference to FIGS. 2, 5, and 6, when the cutting head 18 is in the operating configuration and the cutting head 18 is positioned in a surrounding relationship with the anchor 58, the proximal half portions 36, 38 of the cutting head 18 essentially abut the wall of the anchor 58, and the detent 80 is engaged with the opening 84.

In accordance with the present invention, to engage the cutting head 18 with the anchor 58, the cutting head 18 is moved to a replacement configuration, and the keyed surfaces 28, 30 of the cutting head 18 are aligned with the keyway surfaces 60, 62 of the anchor 58. As intended by the present invention, when the cutting head 18 is in a replacement configuration, the proximal half portions 36, 38 are spaced a small distance further apart than when the cutting head 18 is in the operating configuration.

After the cutting head 18 has been properly aligned with the anchor 58, the cutting head 18 is slid over the anchor 58, and moved to the operating configuration.

In describing the particular method of moving the cutting head 18 to the replacement configuration, the cutting blades 20, 22 are urged toward each other to in turn deflect the proximal half portions 36, 38 away from each other. It may now be appreciated that the slots 32, 34 are formed in the proximal segment 26 of the cutting head 18 to permit the cutting head 18 to be moved to the replacement configuration.

Accordingly, when in the replacement configuration, the cutting head 18 can be slid over the anchor 58, during which procedure the detent 80 will slide against the wall of the anchor 58 until the detent 80 is juxtaposed with the opening 84 of the anchor 58. Because the distal end 76 of the anchor 58 is bevelled, the detent 80 can ride over the bevelled distal end 76 when the cutting head 18 is slid onto the anchor 58.

When the detent 80 is juxtaposed with the opening 84, the detent 80 engages the opening 84 to hold the cutting head 18 stationary with respect to the anchor 58. Then, the blades 20, 22 are released, to establish the operating configuration of the cutting head shown in FIGS. 2 and 5.

Next, an opening is made into the vein 14, and the guide wire 12 is advanced into the vein 14. Then, the valvulotome 10 is slidably engaged with the guide wire 12 and advanced through the opening over the wire 12 and into the vein 14 to cut the valves 16.

Accordingly, in light of the disclosure above the skilled artisan will appreciate that the cutting head 18, having a relatively large diameter D1, e.g., a diameter of about two and eight-tenths millimeters (2.8 mm), can be engaged with the anchor 58 and the valvulotome 10 then advanced over the wire 12 into the saphenous vein 14 in the thigh of the patient. The cutting blades 20, 22 can be viewed by a surgeon on the video display apparatus 70 and aligned as appropriate for cutting one or more of the valves 16.

When the valvulotome 10 is to be advanced further into narrower regions of the vein 14 to cut additional venous valves 16, the valvulotome 10 is retrieved from the vein 14. Next, the cutting head 18 is disengaged from the anchor 58. To disengage the cutting head 18 from the anchor 58, the cutting blades 20, 22 are urged toward each other to in turn deflect the proximal half portions 36, 38 away from each other to establish the replacement configuration for the cutting head 18, and the cutting head 18 is slid off the anchor 58.

Then, another like cutting head (not shown) having a smaller diameter than the cutting head 18 is moved to the replacement configuration and slid over the anchor 58. When the cutting head has been properly aligned with the anchor 58, the blades of the cutting head are released, moving the head into the engaged position wherein the head is fixedly attached to the anchor 58.

Next, the valvulotome 10 can again be advanced into the vein 14 to cut venous valves 16 which are in comparatively narrow portions of the vein 14.

What is claimed is:

1. A method for cutting venous valves in-situ within a vein, comprising the steps of:

making an entry opening into the vein;
   connecting a first cutting head having first and second cutting blades and a proximal segment having a plurality of portions to a pushing member by:
   urging the blades toward each other to cause the portions to move away from each other;
   advancing the cutting head onto the pushing member;
   releasing the blades to permit the blades to move away from each other, thereby causing the portions of the cutting head to engage the pushing member;
   operably engaging the pushing member with an optical scope;
   advancing the pushing member into the vein through the opening in a direction opposite to normal venous blood flow to cut the venous valves with the cutting head and to generate an image of the inside of the vein;
   removing the pushing member from the vein;
   disconnecting the first cutting head from the pushing member without substantially damaging the first cutting head and pushing member; and
   connecting a second cutting head to the pushing member without substantially damaging the second cutting head and pushing member.

* * * * *